United States Patent [19]
Kim et al.

[11] Patent Number: 5,866,377
[45] Date of Patent: Feb. 2, 1999

[54] AMINOOLIGOSACCHARIDE DERIVATIVE AND PROCESS FOR PREPARING THE SAME

[75] Inventors: Jung Woo Kim; Kwang Moo Lee; Hyoung Sik Chun; Jong Gwan Kim; Hung Bae Chang; Sun Ho Kim; Kyeong Bok Min; Kyoung Sik Moon, all of Seoul, Rep. of Korea

[73] Assignee: Chong Kun Dang Corporation, Seoul, Rep. of Korea

[21] Appl. No.: 875,146

[22] PCT Filed: Dec. 30, 1995

[86] PCT No.: PCT/KR95/00184

§ 371 Date: Jun. 30, 1997

§ 102(e) Date: Jun. 30, 1997

[87] PCT Pub. No.: WO96/20945

PCT Pub. Date: Jul. 11, 1996

[30] Foreign Application Priority Data

Dec. 30, 1994 [KR] Rep. of Korea ....................... 94-39755

[51] Int. Cl.[6] .............................. C12P 19/28; C12N 9/99; C12N 1/20; A01N 43/04
[52] U.S. Cl. ......................... 435/85; 435/184; 435/253.5; 514/42
[58] Field of Search ................................. 435/84, 85, 101, 435/184, 200, 201, 209, 253.5; 514/23, 25, 42, 54; 536/1.11, 18.7, 123.1

[56] References Cited

U.S. PATENT DOCUMENTS 4,990,500  2/1991  Vertesy et al. ............................. 514/54

FOREIGN PATENT DOCUMENTS 3-19239  3/1991  Japan .

OTHER PUBLICATIONS

Truscheit et al. "Chemistry and Biochemistry of Microbial alpha–Glucosidase Inhibitors," Angew. Chem. Int. Ed. Engl. (1981) 20: 744–761, 1981.

Carey et al. "Advanced Organic Chemistry. Part B: Reactions and Synthesis," 2nd edition (Plenum Press: New York) (1980) pp. 494–498, 1980.

Shinjuro Namiki, et al., Studies on the α–Glucoside Hydrolase Inhibitor, Adiposin, I. Isolation and Physicochemical Properties, The Journal of Antibiotics, 35:1234–1236 (1982).

Shinjuro Namiki, et al., Studies on the α–Glucoside Hydrolase Inhibitor, Adiposin, II. Taxonomic Studies on the Producing Microorganism, The Journal of Antibiotics, 35:1156–1173 (1982).

Jiro Itoh, et al., Oligostatins, New Antibiotics with Amylase Inhibitory Activity, I. Production, Isolation and Characterization, The Journal of Antibiotics, 34:1424–1428 (1981).

Shoji Omoto, et al., Oligostatins, New Antibiotics with Amylase Inhibitory Activity, II. Structures of Oligostatins D, D and E, The Journal of Antibiotics, 34:1429–1433 (1981).

Kunio Kangouri, et al., Studies on the α–Glucoside Hydrolase Inhibitor, Adiposin, III. α–Glucoside Hydrolase Inhibitory Activity and Antibacterical Activity in Vitro, The Journal of Antibiotics, 35:1160–1166 (1982).

Shinjuro Namiki, et al., Studies on the α–Glucoside Hydrolase Inhibitor, Adiposin, IV. Effect of Adiposin on Intestinal Digestion of Carbohydrates in Experimental Animals, The Journal of Antibiotics, 35:1167–1173 (1982).

H.S. Chun and J.W. Kim, a Novel α–Glucosidase Inhibitor, CKD–711, Proceedings of Seoul Conference on Actinomycetes '97, Research Center for Molecular Microbiology, Seoul National University and Korean Research Group for Actinomycetes, Seoul, Korea, May 23, pp. 23–34 (1997).

D.H. Choung, et al., Determination of the Structure of CK–4416, α–Glucosidase Inhibitors, using Nuclear Magnetic Resonance, Scientific Meeting and General Assembly Commemorating 30th Anniversary, The Biochemical Society of Republic of Korea, Seoul, Korea, May 2–3, p. 83 (1997).

*Primary Examiner*—Jean C. Witz
*Assistant Examiner*—Susan Hanley
*Attorney, Agent, or Firm*—Knobbe, Martens, Olson & Bear, LLP

[57] ABSTRACT

The present invention relates to novel aminooligosaccharide derivative and pharmaceutically acceptable non-toxic salts thereof, which possess potent saccharide hydrolase inhibition and antibacterial activities. The invention also relates to a process for preparing the same and to pharmaceutical compositions containing the same as active ingredients. In accordance with the present invention, the inventors isolated novel aminooligosaccharide derivative from a soil microorganism categorized as *Streptomyces sp.*, and discovered that it can be applied as potent inhibitors for saccharide hydrolases and antibacterial agents as well.

8 Claims, 4 Drawing Sheets

AMINOOLIGOSACCHARIDE DERIVATIVE AND PROCESS FOR PREPARING THE SAME

BACKGROUND OF THE INVENTION

1. Field of the Invention

The present invention relates to novel aminooligosaccharide derivative and pharmaceutically acceptable non-toxic salts thereof, which possess potent saccharide hydrolase inhibition and antibacterial activities. The invention also relates to a process for preparing the same and to pharmaceutical compositions containing the same as active ingredients.

2. Description of the Prior Art

It has been well known that inhibitors of saccharide hydrolases such as amylase and saccharase may be applied in the treatment or prevention of diabetes, hyperlipoproteinemia, hyporlipidemia, obesity or other secondary symptoms caused thereby.

In this regard, several aminooligosaccharide derivatives, for example, A-2396 which is produced by *Streptomyces sp.* A2396(see: Japanese Patent Laid-Open (Sho)54-92909), Oligostatin which is provided by *Streptomyces myxogenes* (see: J. Antibiotics, 34:1424-1433 (1981)), Adiposin (see: J. Antibiotics, 35:1234-1236(1982)) and NS complex which is produced by *Streptomyces flavochromogenes*(see: Japanese Patent Laid-Open (Hei)3-19239), have been reported as potent inhibitors of the saccharide hydrolases.

On the other hand, the NS complex, whose chemical structure is quite similar to the aminooligosaccharide derivative of the invention, is represented by the formula below:

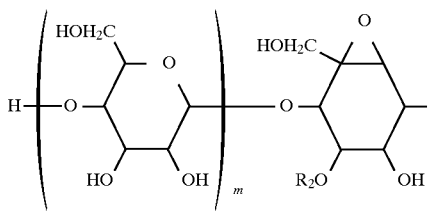

In accordance with the present invention, the inventors isolated novel aminooligosaccharide derivative from a soil microorganism categorized as *Streptomyces sp.*, and discovered that it can be applied as potent inhibitors for saccharide hydrolases and antibacterial agents as well.

SUMMARY OF THE INVENTION

The primary object of the present invention is, therefore, to provide novel aminooligosaccharide derivative, CK-4416 represented by the general formula(I) and salts thereof:

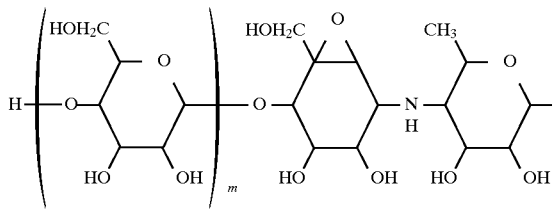
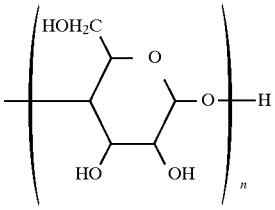
(I)

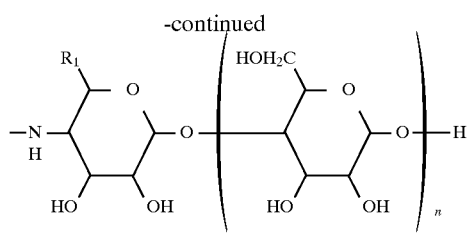

wherein:
  m is an integer of 0 or 1;
  n is an integer of 1 to 4;
  m+n is an integer of 1 to 5;
  $R_1$ is lower alkylhydroxide; and,
  $R_2$ is hydrogen or lower alkyl.

The other object of the invention is to provide the use of aminooligosaccharide derivative as inhibitors of saccharide hydrolases and antibacterial agents.

Another object of the invention is to provide a process for preparing aminooligosaccharide derivative from *Streptomyces sp.* CK-1416.

BRIEF DESCRIPTION Of THE DRAWINGS

The above and the other objects and features of the present invention will become apparent from the following descriptions given in conjunction with the accompanying drawings, in which.

DETAILED DESCRIPTION OF THE INVENTION

Figure 1:
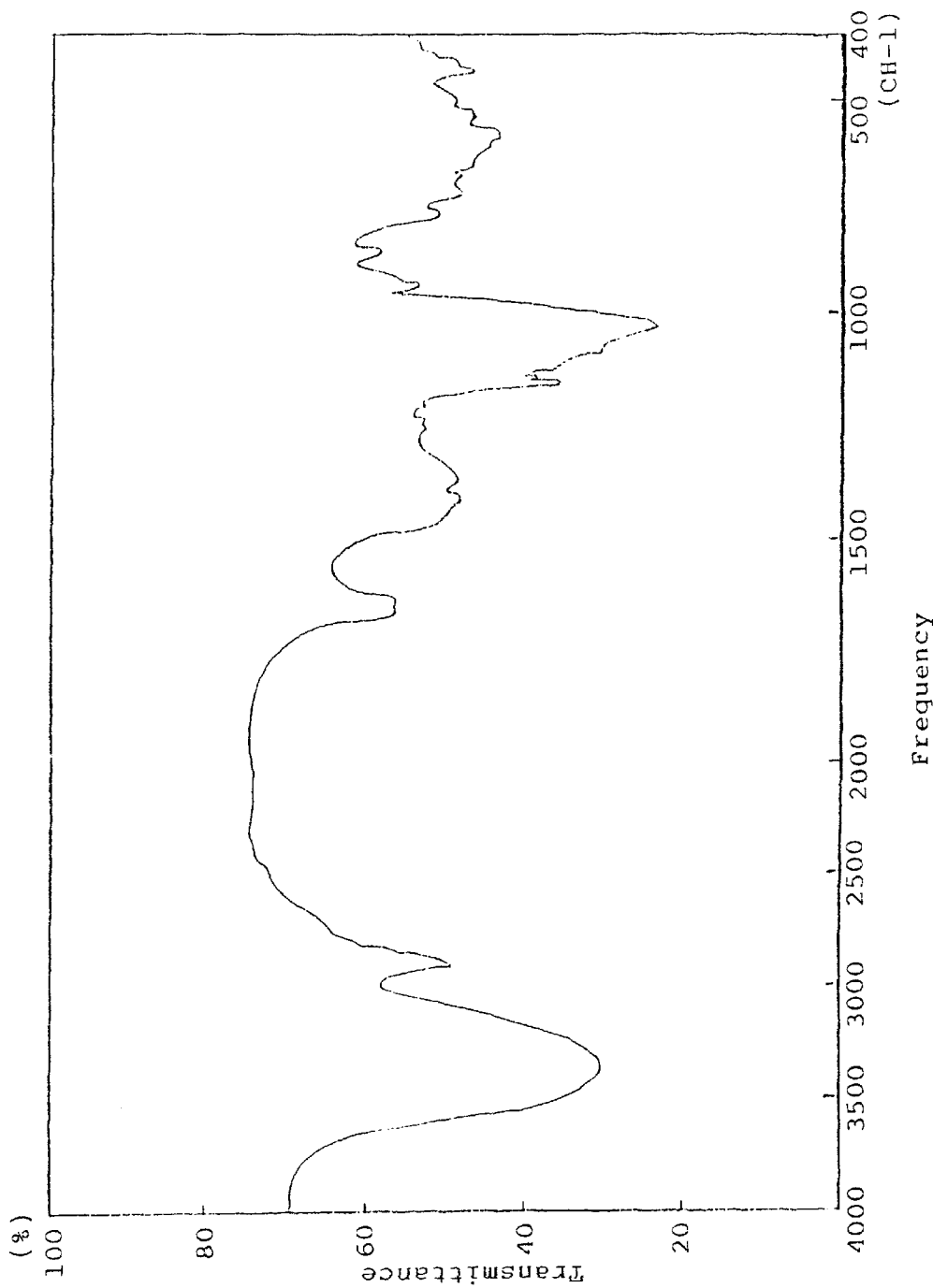
FIG. 1 is a IR spectrum of CK-4416 material of the invention.

The present inventors have screened soil microorganisms to isolate a microbe producing the aminooligosaccharide derivative of the invention. The microbe thus isolated was identified as a species of Streptomyces genus and named as *Streptomyces sp.* CK-4416. In addition, the aminooligosaccharide derivative produced therefrom are determined to be novel one and named as CK-4416.

CK-4416 is produced from *Streptomyces sp.* CK-4416 culturing on a medium containing carbon and nitrogen sources under an aerobic condition employing shaking culture or aerobic spinner culture. As a carbon source, commercially available glucose, glycerin, maltose, starch, sucrose, molasses and dextrin may be utilized; as a nitrogen source, commercially available soybean flour, corn steep liquor, beef extract, cotton seed flour, peptone, wheat germ, fish meal, inorganic ammonium salts and $NaNO_3$, may be utilized; and, $CaCO_3$, NaCl, KCl, $MgSO_4$ and phosphate salts may be utilized as inorganic salts. The medium for culturing *Streptomyces sp.* CK-4416 may further comprise some metal ions such as Fe, Mn and Zn in a trace amount, and antifoaming agent such as plant oils, higher alcohols including octadecanol and silicone compounds, if they are necessary. The medium may also comprise any compound which eases the culture of *Streptomyces sp.* CK-4416 to produce CK-4416 material with a high yield.

*Streptomyces sp.* ClK-4416 is cultured in accordance with conventional methods in the art, which includes solid and liquid culture. Liquid culture is preferably carried out by employing stationary culture, spinner culture, shaking culture and aeration culture, more preferably, shaking culture and submerged aeration culture. Incubation is carried out at the temperature range of 20° to 37° C., more preferably, 25° to 30° C., under a neutral condition of pH 6 to 8, for 24 to 192 hrs, more preferably, 48 to 120 hrs.

CK-4416 is obtained from the culture of *Streptomyces sp.* CK-4416, in accordance with conventional purification methods in the art, employing ion-exchange, adsorption, partition and gel-filtration chromatographies. CK-4416 can also be isolated by high performance liquid chromatography (HPLC) or thin-layer chromatography(TLC).

CK-4416 may be applied in the treatment or prevention of insulin-independent diabetes, hyperlipoproteinemia and obesity caused by hyperlipidemia, or as recovering agent in immunolo-gical depression and it can also be utilized as antibacterial agents.

The present invention is further illustrated in the following examples, which should not be taken to limit the scope of the invention.

EXAMPLE 1

Isolation and identification of *Streptomyces sp.* CK-4416

Screening of soil microorganisms was carried out to isolate the titled microorganism and it was isolated from the forest soil collected in the area of Chochun-Eup, Buk-Kun, Cheju-Do, Korea. The isolated microorganism was characterized as followings.

1. Growth characteristics

Growth Characteristics of the isolated microorganism on a variety of growth media are summarized in Table 1 below.

TABLE 1

Growth Characteristics of *Streptomyces sp.* CK-4416 on a Variety of Agar Media (incubation at 28° C. for 14 days).

| Yeast-Malt Extract Agar (ISP No. 2) | Oatmeal Agar (ISP No. 3) |
|---|---|
| Growth: moderate | Growth: good |
| Aerial mycelium: white, good | Aerial mycelium: grey-yellow, good |
| Vegetative mycelium: yellow-white | Vegetative mycelium: yellow-white |
| Soluble pigment: none | Soluble pigment: none. |
| Inorganic salt-Starch Agar (ISP No. 4) | Glycerin-Asparagine Agar (ISP No. 5) |
| Growth: poor - moderate | Growth: moderate |
| Aerial mycelium: poor | Aerial mycelium: moderate yellow-white |
| Vegetative mycelium: poor, yellow-white | Vegetative mycelium: poor, yellow-white |
| Soluble pigment: none | Soluble pigment: none |
| Peptone-Yeast Iron Agar (ISP No. 6) | Tyrosine Agar (ISP No. 7) |
| Growth: poor | Growth: good |
| Aerial mycelium: none | Aerial mycelium: good |
| Vegetative mycelium: poor | Vegetative mycelium: poor |
| Soluble pigment: none | Soluble pigment: none |
| Sucrose-Nitrate Agar (Waksman No. 1) | Glucose-Asparagine Agar (Waksman No. 2) |
| Growth: poor - moderate | Growth: good |

TABLE 1-continued

Growth Characteristics of *Streptomyces sp.* CK-4416 on a Variety of Agar Media (incubation at 28° C. for 14 days).

| Aerial mycelium: none | Aerial mycelium: grey-white, good |
|---|---|
| Vegetative mycelium: moderate, yellow-white | Vegetative mycelium: poor, grey-brown |
| Soluble pigment: none | Soluble pigment: none |
| Nutrient Agar (Waksman No. 14) | Emerson Agar (Waksman No. 28) |
| Growth: poor | Growth: poor - moderate |
| Aerial mycelium: none | Aerial mycelium: poor |
| Vegetative mycelium: poor, yellow-white | Vegetative mycelium: moderate, fold, yellow-white |
| Soluble pigment: none | Soluble pigment: none |

2. Morphological characteristics

Microscopic examination of *Streptomyces sp.* CK-4416 revealed that: one or three spirals of more than 20 spores per chain which were grown from the ends of aerial mycelium were observed, while verticilated mycelium and fragmentation were not observed. Oval-like spores which have smooth surfaces and range (0.6–0.7)×(0.5–1.0) μm in size were observed, while specific organelles such as sclerotia and sporangia were not observed.

3. Effect of growth temperature(incubation on oatmeal agar for 14 days)

4° C.: No growth

15° C.: Poor growth, No aerial mycelium

20° C.: Poor growth, Poor aerial mycelium

28° C.: Moderate growth, Good aerial mycelium

37° C.: Moderate growth, Good aerial mycelium

45° C.: Moderate growth, Moderate aerial mycelium

55° C.: No growth

4. Physiological characteristics (1) Starch hydrolysis(Starch-inorganic salt agar): (+)

(2) Melanin pigment production: (−)

5. Carbon source assimilability

*Streptomyces sp.* CK-4416 was cultured on Pridham-Gottlieb gar medium(ISP No.9) comprising respective sugars exemplified in Table 2 below under a temperature of 28° C. for 14 days, and carbon source assimilabilities for the sugars were determined.

TABLE 2

Carbon Source Assimilability of *Streptomyces sp.*

| Sugar | Assimilability* |
|---|---|
| no carbon source | ± |
| D-glucose | + |
| L-arabinose | ++ |
| sorbitol | ± |
| D(+)-raffinose | ++ |
| inositol | ± |
| D-xylose | + |
| β-D(−)-fructose | ++ |
| D(+)-mannose | + |
| L(−)-sorbose | − |
| sucrose | ++ |
| α-L-rhamnose | − |

−: No Growth
+: Moderate Growth
±: Poor Growth
++: Good Growth

6. Cell wall composition

LL-diaminopimellic acid and glycine were detected in the cell wall fraction of *Streptomyces sp.* CK-4416.

From the studies on the growth, morphology, physiology and carbon source assimilability of the microorganism isolated in the invention, the microorganism is finally identified as Streptomyces genus which has not reported in the art. Accordingly, the novel microorganism was named as *Streptomyces sp.* CK-4416 and deposited in the Korean Collection for Type Culture(KCTC) located at KRIBB, KIST, PO Box 115, Yusong-Ku, Taejon, 305-600, Korea, an international depository authority(IDA) under an accession No. KCTC 0131 BP on Nov. 30, 1994 under the terms of the Budapest Treaty.

EXAMPLE 2

Culture of *Streptomyces sp.* CK-41416

To four of 500 ml Erlenmeyer flasks was addled 100 ml of a medium for seed culture(pH 6.5) containing glucose 1 (w/v) %, dextrin 1 (w/v) %, NZ-amine(type A) 0.5 (w/v) %, yeast extract 0.5 (w/v) % and calcium carbonate 0.1 (w/v) %, and sterilized at 120° C. for 15 min. 1 platinum loop of slant culture of *Streptomyces sp.* CK-4416 which was obtained from a subculture, was inoculated to each of four flasks and incubated under shaking at 27° C. for 3 days. Then, 100 ml of culture media(pH 6.5) containing soluble starch 3 (w/v) %, soybean powder 1.5 (w/v) %, corn steep liquor 1.5 (w/v) %, polypeptone 0.2 (w/v) %, $Na_2S_2O_3$ 0.1 (w/v) %, calcium carbonate 0.5 (w/v) %, cobalt chloride 0.0001 (w/v) % was added to 200 of 500 ml Erlenmeyer flasks and sterilized at 120° C. for 30 min. 2 (v/v) % of seed culture was inoculated to the media and incubated at 27° C. for 3 days under shaking at 240 rpm. CK-4416 was quantitatively assayed by the determination of antimicrobial activity employing a test organism *Comamonas terrigena* (ATCC 8461) in accordance with conventional paper disc method. After 3 days culture, pH and yield were determined as 7.2 and 0.06 mg/ml, respectively.

EXAMPLE 3

Isolation of CK-4416 material(I)

18 L of the culture obtained from Example 2 was centrifuged to remove cell pellets, and 14 L of supernatant was collected. The supernatant was adjusted its acidity to pH 3.1, applied onto a 6 cm×30 cm column packed at a flow rate of 50 ml/min, with an activated carbon(Wako Junyaku, Japan) which is an adsorption resin, washed with 5 L of distilled water, and eluted with 50 (v/v) % methanol. As the elute was fractionated by 400 ml, CK-4416 was eluted from fraction Nos. 3 to 6. These fractions were pooled and concentrated under a reduced pressure to give 14 g of a yellow oily material. The material was dissolved in 50 ml of distilled water and its acidity was adjusted to pH 3.1. The resultant was applied onto a 6 cm×30 cm column packed with Sp-Sephadex($H^+$) available from Sigma Chemical Co., U.S.A. at a flow rate of 20 ml/min, washed with 5 L of distilled water, and eluted with a 1N ammonia water. As the elute was fractionated by 400 ml, the fractions containing CK-4416 compound were eluted from fraction Nos. 3 to 4. These fractions were pooled and concentrated under a reduced pressure and dried to give 1 g of a yellow powder. Then, the powder was dissolved in 30 ml of distilled water. The resultant was adjusted its acidity to pH 3.1, applied to a column(3 cm×40 cm) packed with Dowex 50 W-8X (pyridine salt) available from Sigma Chemical Co., U.S.A. at a flow rate of 5 ml/min, washed with 2 L of distilled water, and eluted with 3 L of pyridine-formic acid buffer solution (pH 3.1) with a gradient of 0 to 0.2M. As the elute was fractionated by 15 ml, substance A was eluted from fraction Nos. 79 to 120 and substance B from fraction Nos. 129 to 159, respectively. Each of the elutes was concentrated under a reduced pressure to give 500 mg of substance A and 90 mg of substance B as pale yellow powder, respectively.

EXAMPLE 4

Isolation of CK-4416 material(II)

The substance A obtained from Example 3 was dissolved in 4 ml of distilled water, applied to a 3 cm×50 cm column packed with Sephadex G-10 available from Sigma Chemical Co., U.S.A., and eluted with water. As the elute was fractionated by 5 ml, an active material was eluted from fraction Nos. 39 to 45. These fractions were concentrated and dried to give 390 mg of white powder. Similarly, the substance B obtained from Example 3 was treated to give 50 mg of white powder.

EXAMPLE 5

Isolation of CK-4416 material(III)

60 mg of the substance A obtained from Example 4 was applied to a preparative high performance liquid chromatography (column: Tosoh Amide-80, solvent: 60 (v/v) % acetonitrile) available from Shimadzu, Japan. Among the substances represented by the general formula(I), a substance of the formula(I) in which m=1, n=2, $R_1$=methylhydroxide and $R_2$=hydrogen; a substance of the formula(I) in which m=0, n=4, $R_1$=methylhydroxide and $R_2$=hydrogen; and a substance of the formula(I) in which m=1, n=3, $R_1$=methylhydroxide and $R_2$=hydrogen were subsequently eluted. Theses three elutes were concentrated under a reduced pressure and freeze-dried to give 5 mg, 45 mg and 3 mg as white powder, respectively.

30 mg of the substance B obtained from Example 4 was taken and treated in the same manner under the same conditions. Among the substances represented by the formula(I), 10 mg of a substance of the formula(I) in which m=0, n=2, $R_1$=methyl hydroxide and $R_2$=hydrogen; 7 mg of a substance of the formula(I) in which m=1, n=1, $R_1$=methylhydroxide and $R_2$=hydrogen; and 8 mg of a substance of the formula(I) in which m=0, n=3, $R_1$=methylhydroxide and $R_2$=hydrogen were obtained, respectively.

EXAMPLE 6

Identification of CN-4416 compound

CK-4416 compound was identified by determining physico-chemical characteristics of the oligosaccharide derivative of the formula(I), with a compound in which m=0, n=4, $R_1$=methyl hydroxide and $R_2$=hydrogen by employing physical and chemical analysis methods.

1. Color and type:

white powder

2. Elemental analysis (%):

|  | Carbon | Hydrogen | Nitrogen |
|---|---|---|---|
| (Analyzed) | 44.31 | 6.32 | 1.36 |
| (Calculated) | 44.35 | 6.33 | 1.39 |

3. Molecular formula:

$C_{37}H_{63}NO_{30}$

Figure 4:
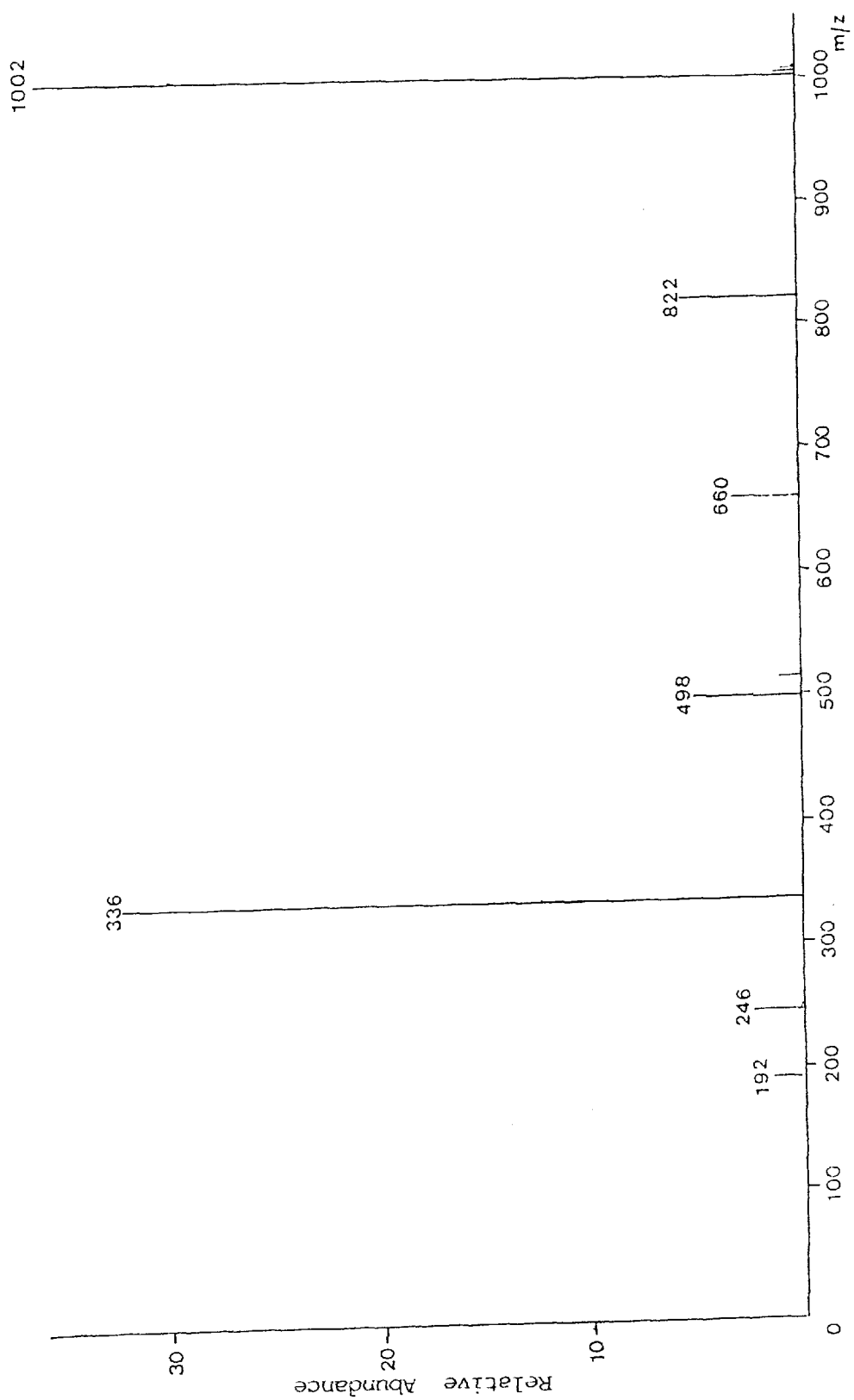
FIG. 4 is a FAB-MS/MS spectrum of CK-4416.

4. Molecular weight:

1,001.9 FAB-MS/MS$(M+H)^+$1002(see: FIG. 4)

Figure 2:
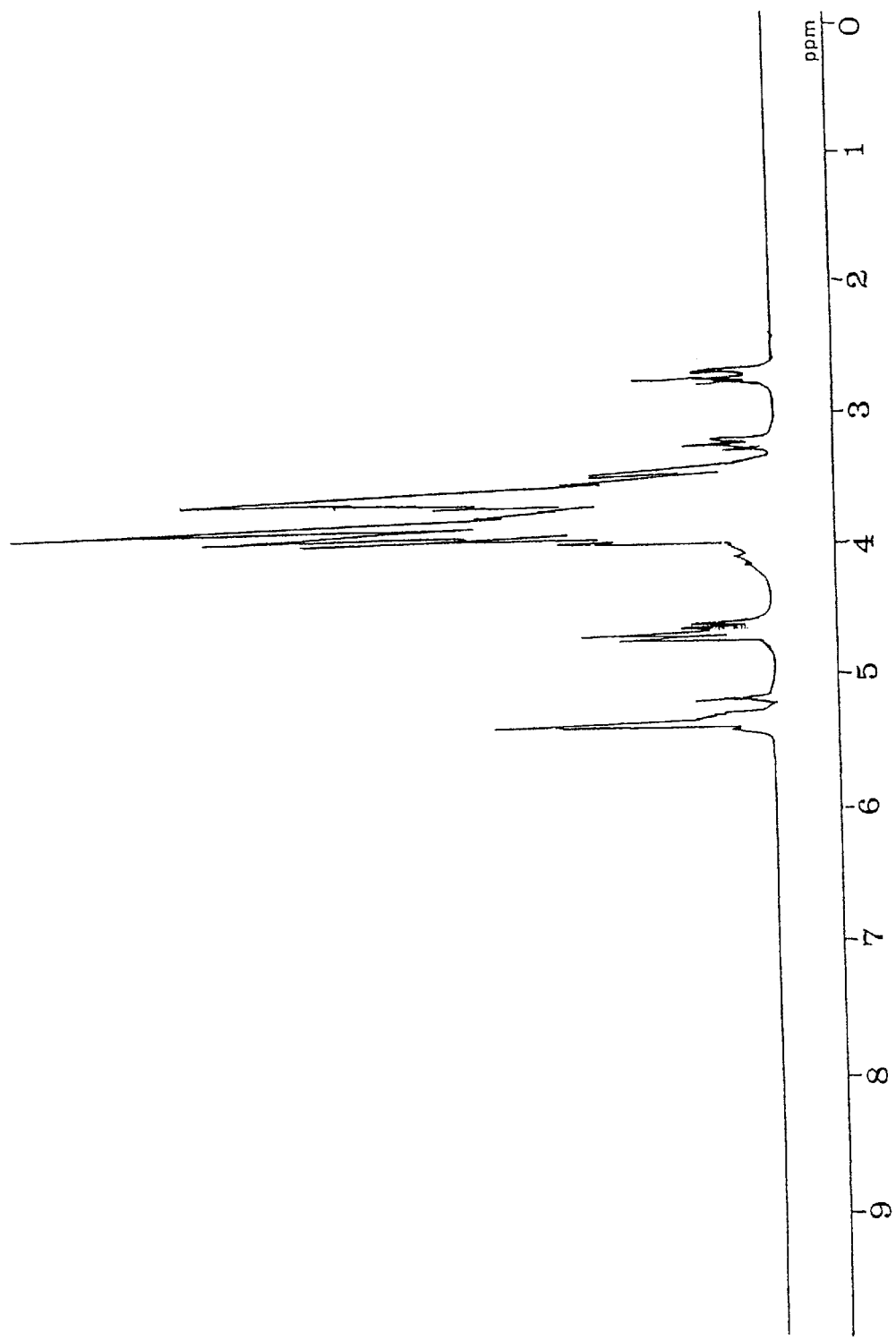
FIG. 2 is a $^1$H-NMR spectrum of CK-4416.
Figure 3:
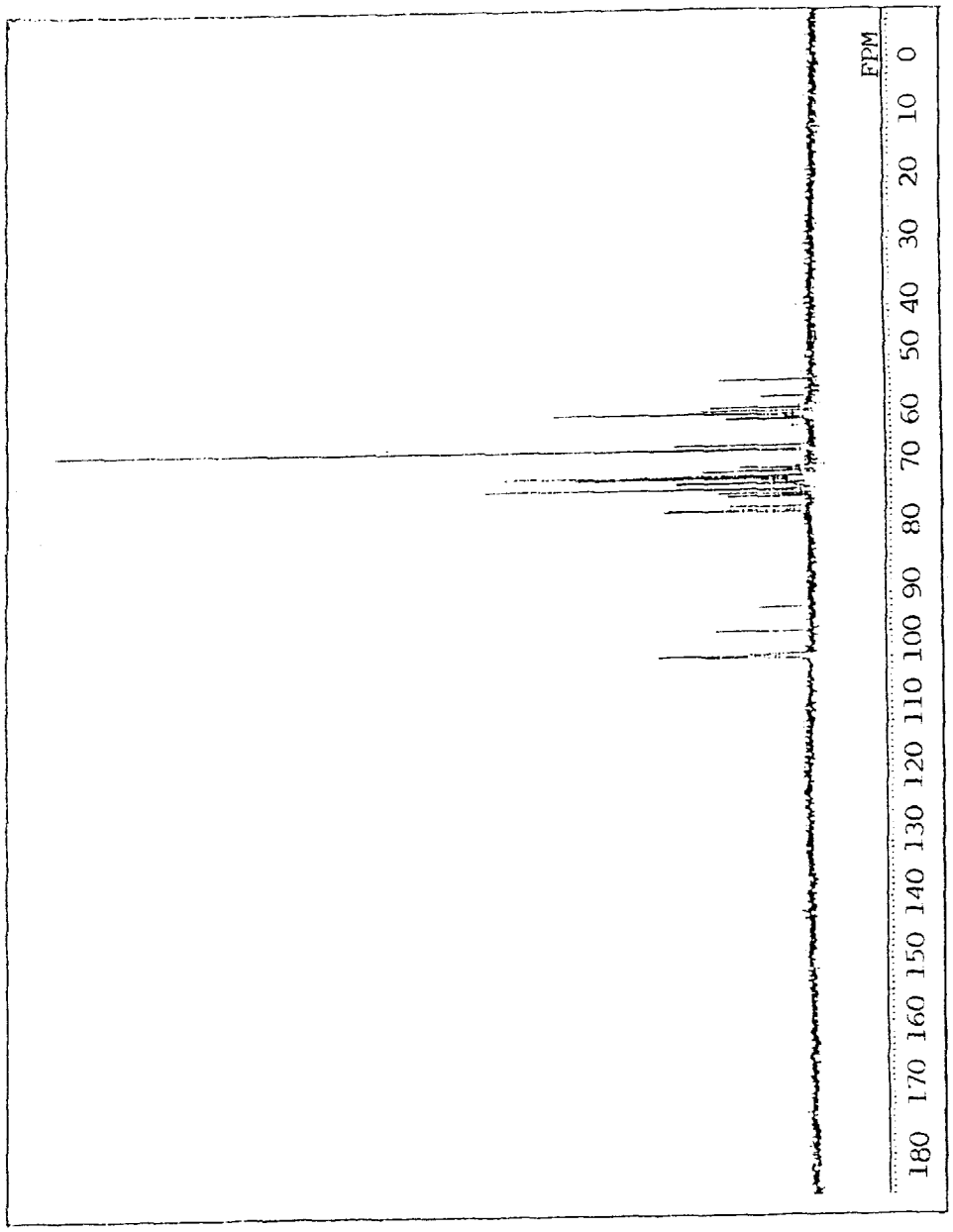
FIG. 3 is a $^{13}$C-NMR spectrum of CK-4416.

5. Melting point:
162° C.
6. Specific rotation:
$[\alpha]_D = +146°$ (c 0.1 in $H_2O$)
7. UV absorption spectrum (solvent: water, conc.=0.1 mg/ml):
end absorption is observed
8. IR spectrum:
IR spectrum measured by KBr method(see: FIG. 1) main wavelengths($cm^{-1}$): 3,400; 2,900; 1,630; 1,410; 1,390; and 1,050
9. $^1$H-NMR spectrum:
$^1$H-NMR spectrum measured in $D_2O$(see: FIG. 2)
10. $^{13}$C-NMR spectrum:
$^{13}$C-NMR spectrum measured in $D_2O$(see: FIG. 3)
11. Solubility:
soluble in water and ethanol insoluble in benzene and normal hexane
12. Color reaction:
positive in silver nitrate-sodium hydroxide, Somoginelson, and permanganate reactions; and
negative in ninhydrin and Sakaguchi reactions
13. Acidic, neutral or basic properties:
weakly basic
14. TLC:
$R_f$: 0.14; [Tokyo Kasei K.K., silica gel f(S201), Japan] developing solvent: ethylacetate-methanol-water=5:3:2 (v/v/v)

In addition, it was further identified that a compound of the formula(I) in which m=0, n=2, $R_1$=methylhydroxide and $R_2$=hydrogen has a molecular formula of $C_{25}H_{43}NO_{20}$, and a molecular weight of 677.6111; a compound of the formula (I) in which m=1, n=1, $R_1$=methylhydroxide and $R_2$=hydrogen has a molecular formula of $C_{25}H_{43}NO_{20}$, and a molecular weight of 677.6111; a compound of the formula (I) in which m=0, n=3, $R_1$=methyl hydroxide and $R_2$=hydrogen has a molecular formula of $C_{31}H_{53}NO_{25}$, and a molecular weight of 839.7514; a compound of the formula (I) in which m=1, n=2, $R_1$=methylhydroxide and $R_2$=hydrogen has a molecular formula of $C_{31}H_{53}NO_{25}$, and a molecular weight of 839.7514; and a compound of the formula(I) in which m=1, n=3, $R_1$=methylhydroxide and $R_2$=hydrogen has a molecular formula of $C_{37}H_{63}NO_{30}$, and a molecular weight of 1,001.8934.

From the analysis results above, it was determined that the aminooligosaccharide derivative of the invention is novel compound.

EXAMPLE 7

Biological activities of CK-4416

Biological activities of CK-4416 were determined, with an aminooligosaccharide compound represented by the formula(I) wherein m=0, n=4, $R_1$=methylhydroxide and $R_2$=hydrogen.

EXAMPLE 7-1

Antibacterial activity

Antibacterial activities for Gram-positive and negative bacterial strains were determined with 1 mg/ml of CK-4416 sample, by employing paper disc method. From the results, no activity was observed for Gram-positive, while 24.8 mm of inhibitory zone was showed for Gram-negative bacterial strain, i.e., *Comamonas terrigena*(ATCG 8461).

EXAMPLE 7-2

Inhibition of amylase activity

An enzyme solution(hereinafter referred to as 'solution A') containing amylase dissolved in 0.25M phosphate buffer(pH 7.0), 0.25M phosphate buffer solution(pH 7.0) (hereinafter referred to as 'solution B') and 0.04 (w/v) % starch solution (hereinafter referred to as 'solution C') were prepared, respectively. Then, 0.05 ml of solution B containing CK-4416 dissolved in solution B, 0.1 ml of solution B and 0.05 ml of solution B were combined to incubate at 37° C. for 5 min, and further incubated for 30 min after the addition of 0.5 ml of solution C. After invention, absorbance at 660 nm was deter-mined for CK-4416 sample(T) and control(C) which is free of sample. Finally, half(50%) inhibition ratio for amylase activity($IC_{50}$) was determined as $1.6 \times 10^{-6}$M, when calculated from the equation below.

Inhibition ratio=(C−T)/C×100

EXAMPLE 7-3

Lowering of sugar level in blood

To two groups of 5 male SD rats fasted for 12 hrs, 1.5 g/kg of starch was orally administered, concurrently with 40 mg/kg and 80 mg/kg of samples. Then, blood was taken from the rats after 1 hr from administration, and glucose level in blood was determined by glucose oxidase method and compared with control group which has not taken the CK-4416 sample. The results were illustrated in Table 3 below. As can be seen in Table 3, it was clearly determined that CK-4416 of the invention is able to lower sugar level in blood, more than any other aminooligosaccharide compounds previously reported in the art, e.g., NS-complex.

TABLE 3

| Lowering of blood sugar level | |
|---|---|
| | Blood glucose level |
| Control | 124.6 ± 10.2 |
| CK-4416 | |
| 40 mg/kg | 97.5 ± 14.3 |
| 80 mg/kg | 87.5 ± 11.3 |

EXAMPLE 7-4

Toxicity

The acute toxicity tests for CK-4416 were carried out after oral administration of 1 g/kg CK-4416 into 5 ICR mice, which were observed for 14 days. The result reveals that all of the mice were survived.

Pharmaceutically acceptable salts are formed by conventional techniques involving reaction of the compounds of formula(I) with alkali(Na, K) and alkaline earth(Ca, Ba, Zn, Mn) metal bases, more preferably, with alkali metal bases such as, for example, dilute solutions of sodium hydroxide and potassium carbonate. Also, pharmaceutically acceptable salts are formed by conventional techniques involving reaction with amines such as, for example, triethylamine, dibenzylamine, triethanolamine, ethanolamine, N,N'-dibenzylethylenediamine, procaine and equivalent amines.

The compounds of the present invention can be formulated by any of the known appropriate methods with a pharmaceuti-cally acceptable carrier and, if necessary, an adjuvant. For oral administration, for instance, the compounds of the present invention can be formulated into a solid preparation such as tablets, pills, granules, powder, capsules and the like, or a liquid preparation such as solution, suspension, emulsion and the like. When the preparation is used for parental adminis-tration, the preparation is made in an injection formula, an intravenous drip infusion and the like. For the preparation of an injection formula, the compound is preferably dissolved in distilled water or an aqueous solution of a salt such as sodium chloride. For the preparation of an intravenous drip infusion, the compound may be dissolved in a suitable fluid therapy such as a physiological saline, a glucose-sodium chloride solution and the like.

The quantity of active component, that is the compounds of formula(I) according to the present invention, in the pharmaceutical composition and unit dosage form thereof may be varied or adjusted widely depending upon the particular application, the potency of the particular compound, the desired concentration. Generally, the quantity of active component will range between 0.5% to 90% by weight of the composition.

The effective dosage of the compounds of the present invention may vary with the physical condition of the patients. In general, it has been shown advantageous to administer the active compounds in an amount of about 50 to 1000 mg per 1 m² body surface area in order to achieve the desired result.

What is claimed is:

1. An aminooligosaccharide of formula (I) or a pharmaceutically acceptable salt thereof:

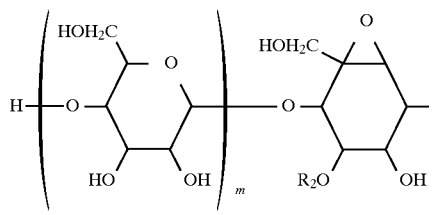

(I)

-continued

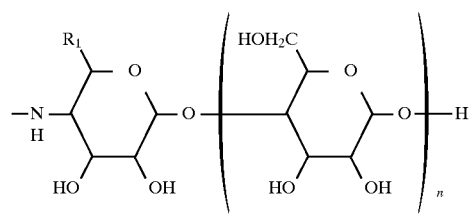

wherein m is an integer of 0 or 1; n is an integer of 1 to 4; m+n is an integer of 1 to 5; $R^1$ is a lower alkylhydroxide; and $R^2$ is a hydrogen or a lower alkyl.

2. An inhibitor of saccharide hydrolase, comprising an aminooligosaccharide according to claim 1 in an amount effective to inhibit activity of saccharide hydrolase.

3. An antibacterial agent comprising an aminooligosaccharide according to claim 1 in an amount effective to suppress bacterial activity.

4. A process for preparing an aminooligosaccharide according to claim 1, which comprises the steps of culturing *Streptomyces sp.* having accession number KCTC 0131BP to produce the aminooligosaccharide; and recovering the aminooligosaccharide.

5. A method for inhibiting saccharide hydrolase, comprising contacting the aminooligosaccharide according to claim 1 with said saccharide hydrolase.

6. A method for suppressing activity of bacteria, comprising contacting the aminooligosaccharide according to claim 1 with said bacteria.

7. The aminooligosaccharide according to claim 1, which is produced by *Streptomyces sp.* having accession number KCTC 0131BP.

8. The aminooligosaccharide according to claim 1, wherein m is 0, n is 2, $R^1$ is methylhydroxide, and $R^2$ is a hydrogen.

* * * * *